United States Patent

Peterson et al.

(10) Patent No.: US 6,575,978 B2
(45) Date of Patent: Jun. 10, 2003

(54) CIRCUMFERENTIAL RESECTING REAMER TOOL

(75) Inventors: Francis C. Peterson, Prescott, WI (US); Todd Bjork, River Falls, WI (US)

(73) Assignee: Spineology, Inc., Stillwater, MN (US)

( * ) Notice: Subject to any disclaimer, the term of this patent is extended or adjusted under 35 U.S.C. 154(b) by 112 days.

(21) Appl. No.: 09/827,202

(22) Filed: Apr. 5, 2001

(65) Prior Publication Data

US 2002/0173813 A1 Nov. 21, 2002

(51) Int. Cl.⁷ ................................................ A61B 17/32
(52) U.S. Cl. ............................ 606/83; 606/84; 606/171
(58) Field of Search ................................ 606/170, 171, 606/172, 173, 79, 86, 80, 81, 82, 83, 84, 85, 167, 180

(56) References Cited

U.S. PATENT DOCUMENTS

| | | | | |
|---|---|---|---|---|
| 5,112,346 A | * | 5/1992 | Hiltebrandt et al. | 606/170 |
| 5,571,131 A | * | 11/1996 | Ek et al. | 606/167 |
| 5,571,189 A | | 11/1996 | Kuslich | 623/17 |
| 5,649,947 A | * | 7/1997 | Auerbach et al. | 600/565 |
| 5,755,979 A | | 5/1998 | Baumgartner | 623/17 |
| 5,817,119 A | * | 10/1998 | Klieman et al. | 606/170 |
| 5,840,044 A | * | 11/1998 | Dassa et al. | 600/567 |
| 5,913,866 A | * | 6/1999 | Ginn et al. | 606/170 |
| 5,928,239 A | | 7/1999 | Sohail | 606/79 |
| 5,972,015 A | | 10/1999 | Schribner et al. | |
| 5,984,939 A | * | 11/1999 | Yoon | 606/139 |
| 6,127,597 A | | 10/2000 | Beyar et al. | 623/16 |

FOREIGN PATENT DOCUMENTS

| | | |
|---|---|---|
| DE | 28 08 911 | 3/1979 |
| DE | 87 12 271 | 3/1988 |
| DE | 37 41 493 A1 | 6/1989 |
| DE | 198 52 682 A1 | 5/2000 |
| WO | 99/02108 | 1/1999 |
| WO | 00/67650 | 11/2000 |

* cited by examiner

*Primary Examiner*—Danny Worrell
(74) *Attorney, Agent, or Firm*—Vidas, Arrett & Steinkraus P.A.

(57) ABSTRACT

A tool for cutting tissue comprising a body, a handle lever, a drive rod, and a cutter beam. The drive rod constructed and arranged for longitudinal movement through the body. The handle lever being operatively engaged to the drive rod, such that when the handle lever is moved between a first position and a second position the drive rod is moved between an advanced position and a retracted position. The drive rod extending from a proximal end of the body to a distal end. The cutter beam being pivotally engaged to the distal end of the body. The cutter beam being pivotally moveable between a non-actuated position and an actuated position. A lower pivot member pivotally connects the distal end of the body and the cutter beam. The cutter beam being further pivotally engaged to a distal end of the drive rod.

14 Claims, 9 Drawing Sheets

CIRCUMFERENTIAL RESECTING REAMER TOOL

CROSS-REFERENCE TO RELATED APPLICATIONS

Not Applicable

STATEMENT REGARDING FEDERALLY SPONSORED RESEARCH

Not Applicable

BACKGROUND OF THE INVENTION

1. Field of the Invention

This invention relates to an apparatus and method for removing, debriding and/or resecting tissue fragments from a body cavity. In particular, the present invention is directed for use in medical procedures where it may be necessary to remove tissue from a body region. The apparatus and method of the present invention may be especially useful in medical procedures such as orthopedic surgery.

2. Description of the Related Art

Medical procedures involving the removal of tissue from a bone or other region of a body are well known in the art. Of particular interest to the present invention are procedures relating to removal of diseased or damaged tissue of a spinal disk, such as a discectomy.

The spinal disc consists of two types of tissues: the nucleus, and the annulus. The annulus is further divided into the inner and outer annulus. Disc hernias usually consist of a bulge of the nucleus and inner annulus through a rent in a small area of the outer annulus. Partial discectomies are frequently performed when a disc herniation causes pressure on a spinal nerve. The operation consists of removal of the herniated nucleus and portions of the inner annulus. In the past surgeons have used a variety of tools to remove spinal disc tissue during a discectomy.

The simplest tools for disc removal are the scalpel and tweezer-type "pick-ups," which are well known in the art. These tools are very inefficient, as the stringy annular tissues tend to simply move aside and remain attached when these tools are used. Scalpels and pick-ups tend to leave behind fragments of tissue. These fragments can lead to re-herniation—a painful condition that might require a second or even a third operation.

So-called "pituitary rongeurs" and "curettes" are the most frequently utilized instruments. Some examples of these instruments may be seen in the following U.S. Patent references:

| U.S. Pat. No. | Inventor(s): |
|---|---|
| 6,200,320 B1 | Michelson |
| 6,142,997 | Michelson |
| 5,961,531 | Weber et al. |
| 5,766,177 | Lucas-Dean et al. |
| 5,653,713 | Michelson |
| 5,484,441 | Koros et al. |
| 5,451,227 | Michaelson |
| 5,312,407 | Carter |
| 5,026,375 | Linovitz et al. |
| 5,061,269 | Muller |
| 4,990,148 | Worrick, III et al. |
| 4,777,948 | Wright |

-continued

| U.S. Pat. No. | Inventor(s): |
|---|---|
| 4,733,663 | Farely |
| 4,722,338 | Wright et al. |
| 3,902,498 | Niederer |
| 3,628,524 | Jamshidi |
| 2,984,241 | Carlson |

Tools, such as those described in the above cited references, while useful, were not specifically designed to remove disc tissue, and tend to require multiple passes to completely clean out the inner annulus tissue. The use of rongeurs and curettes also tends to leave behind fragments of tissue that may also lead to re-herniation. Furthermore, because these rongeurs and curettes require multiple passes, the operation may be prolonged, possibly leading to increased bleeding and higher infection rates.

Many pituitary rongeurs utilize a single cutting blade at the end of a single, unopposed beam. Actuation of the beam, by means of a drive rod, tends to force the distal shaft to move away from the tissue being cut. An open section in the middle of the beam helps reduce this movement, but does not effectively eliminate the unwanted movement.

Other methods and devices which have been developed in order to improve the effectiveness of a disc removal operation include electrical and laser based cautery. While electrical cautery does effectively destroy disc tissue, it produces heat and smoke in the process. Heat can injure surrounding tissue, including delicate spinal nerves, potentially causing further harm to the patient. In addition, the production of smoke may obscure vision and interfere with the surgeons ability to properly perform the operation. Laser cautery like electrical cautery methods also produce heat and smoke. Low energy lasers tend to be less effective and therefore the disc removal procedure can be prolonged and less than complete. Higher energy lasers produce more heat and smoke and therefore can lead to tissue damage beyond the area of intended removal.

Other devices such as low and high-speed pneumatic or electrical powered rotary burrs are also used. But while they are very useful for removing hard tissues, such as bone, they do not efficiently and effectively remove soft tissues, such as disc material. An example of such a rotary burr is shown in U.S. Pat. No. 5,490,860 to Middle et al., the entire contents of which being incorporated herein by reference. Another type of rotary burr is commercially available and is sold under the name Disc Whisk™ available from Surgical Dynamics Inc. of Norwalk, Conn. Rotary burrs attempt to automate and improve the efficiency of disc removal, but these motorized devices are potentially dangerous when used around the spinal cord and spinal nerves as they develop heat, may grab soft tissue and may penetrate too far.

In light of the above it is clear that there remains a need for an improved, hand-powered tool specifically designed for the removal of diseased soft tissue, such as disc tissue. The current invention improves on the current state of the art by providing a apparatus and method which may be used to efficiently, effectively and safely remove soft tissue from a spinal member such as a disk.

BRIEF SUMMARY OF THE INVENTION

The present invention is directed to a unique reamer tool that may be used to circumferentially resect tissue from a diseased area of a body. The reamer tool of the present invention consists of a sturdy, yet small diameter, hand powered, multi-bladed cutting tool and its method of use.

In at least one embodiment of the invention the reamer tool has a cutting beam which is pivotally engaged to the tool assembly, a push rod and handle in a rack and pinion relationship to allow the cutter beam to be pivoted relative to the distal end of the tool assembly. The cutter beam may have a plurality of cutting blades or surfaces. As the cutter beam is pivoted as a result of compression of the handle, the cutting blades cut into and resect the surrounding tissue.

In at least one embodiment of the invention the reamer tool may be equipped with a variety of devices designed to make the surgical procedure more efficient. For example the reamer tool may have an attached or integrated suction tube which may be used to remove the tissue which has been resected by the cutting action of the cutter beam. Other devices may also be employed.

BRIEF DESCRIPTION OF THE SEVERAL VIEWS OF THE DRAWINGS

A detailed description of the invention is hereafter described with specific reference being made to the drawings in which.

DETAILED DESCRIPTION OF THE INVENTION

Figure 1:
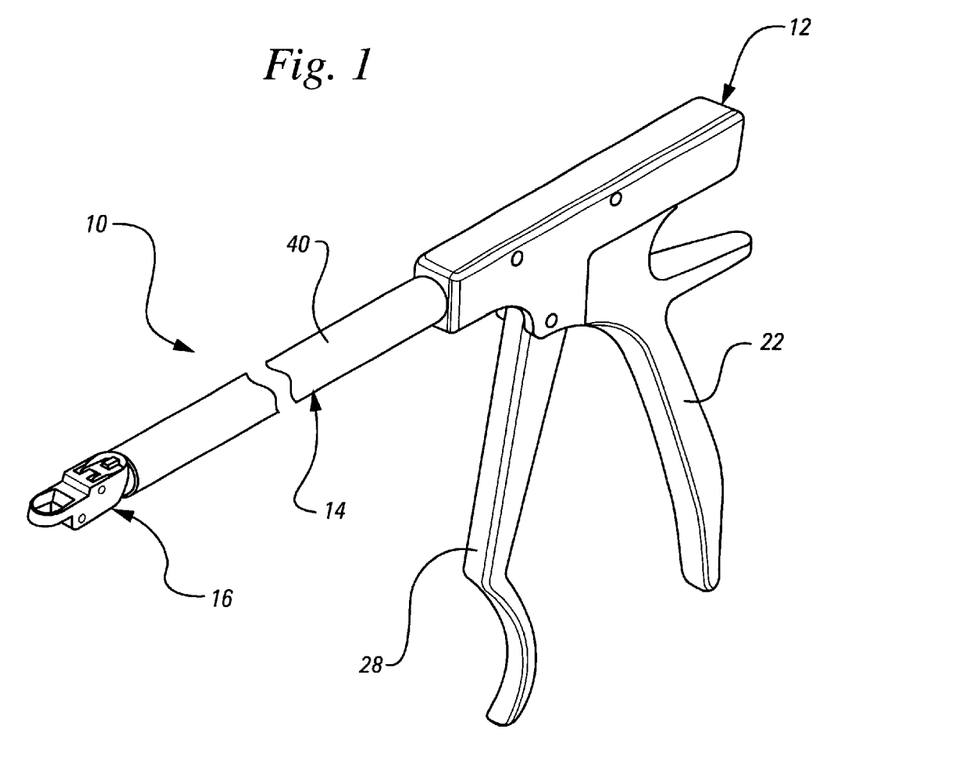
FIG. 1 is a perspective view of an embodiment of the invention.

As may be seen in FIG. 1 the reamer tool, indicated generally at 10 may be thought of as being comprised of three main portions: a proximal portion 12, a middle portion 14, and a distal portion 16.

Figure 2:
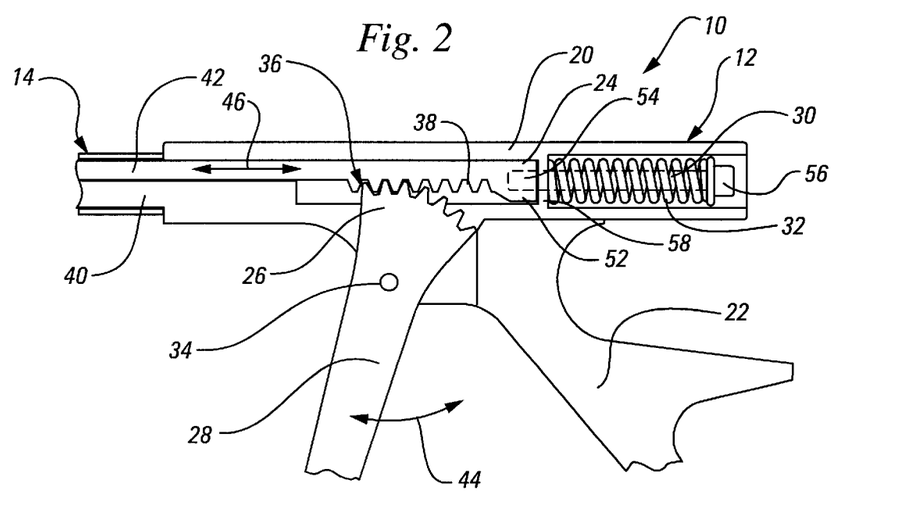
FIG. 2 is a cut-away side view of an embodiment of the invention in the non-actuated position.
Figure 3:
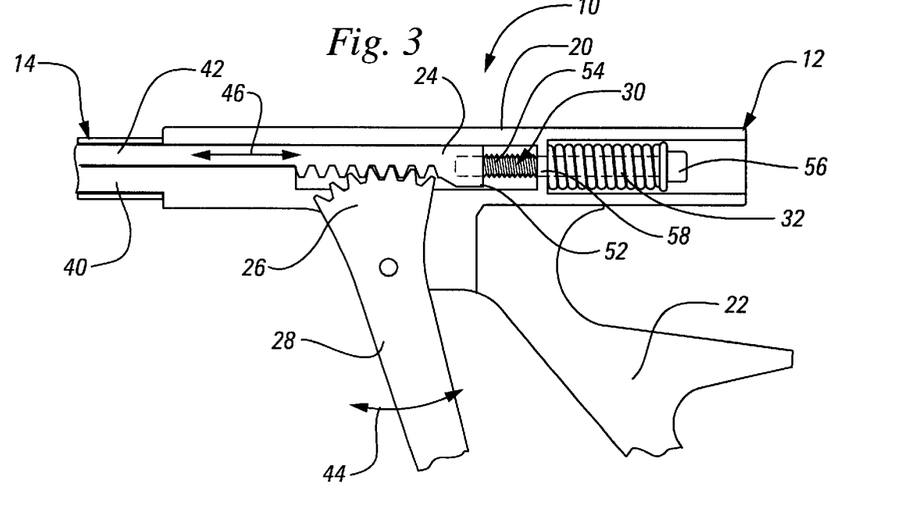
FIG. 3 is a cut-away side view of the embodiment of the invention shown in FIG. 2 in the actuated position.

As may be seen in FIGS. 2 and 3, the proximal or handle portion 12 consists of a handle body 20, a handle body lever 22, a rack 24 and pinion 26, a pinion handle lever 28, a shoulder bolt 30, and a biasing member or return spring 32. The middle portion 14 consists of a shaft tube 40 through which a drive rod 42 is longitudinally actuated. The drive rod 42 is engaged to the distal end 50 (as may be seen in FIG. 4) of the rack 24. When a gripping action supplied by a user (not shown) pivotally actuates the pinion handle lever 28 about the pivot member 34, the teeth 36 of the pinion 26 engage the teeth 38 of the rack 24 resulting in the back an forth movement of the drive rod 42 within the shaft tube 40. As indicated by arrows 44 and 46 the actuation of the pinion handle lever 28 resulting from a compressive force supplied by a user will move the drive rod 42 distally such as shown in FIG. 3, or proximally when the force is removed, as is shown in FIG. 2. The position of the pinion handle lever 28 relative to the handle lever 22, and thus the position of the drive rod 42, will depend on the extent of the compressive force supplied by a user to the pinion handle lever 28 and handle body lever 22.

In FIG. 2 the reamer 10 is shown in the at rest or non-actuated position. The shoulder bolt 30 is engaged to the proximal end 52 of the rack 24. The biasing member or return spring 32 is disposed about a bolt shaft 54 which extends proximally from the rack 24 passing through a return member 58. The bolt shaft 54 ends in an enlarged spring retaining portion 56 of the shoulder bolt 30. The return spring 32 is biasedly engaged between the spring retaining portion 56 of the shoulder bolt 30 and the return member 58. This return spring exerts a force sufficient to keep the drive rod 42 extended distally. The force exerted by the return spring 32 is overcome when the pinion handle lever 28 is engaged by the gripping action of the user previously described and shown in FIG. 3. When the user's grip is relaxed the force exerted by the return spring 32 against the spring retaining portion 56 and the return member 58 will place the reamer back in the at rest position shown in FIG. 2. The tool is returned to the rest position so that its profile is small enough to be removed from a guide tube or a hole in bone.

The lever may be actuated by an air cylinder, an electric solenoid or any other actuator means. Hand operated levers are shown which are less expensive and easier to clean.

Figure 7:
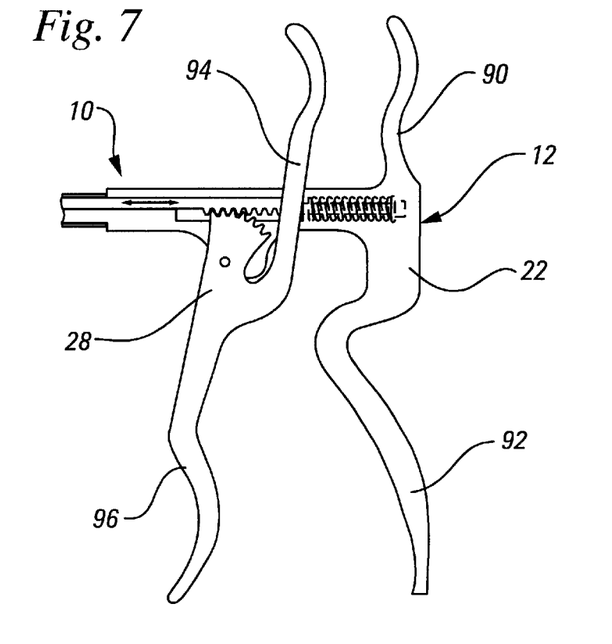
FIG. 7 is a cut-away side view of a two handed embodiment of the invention in a non-actuated position.
Figure 8:
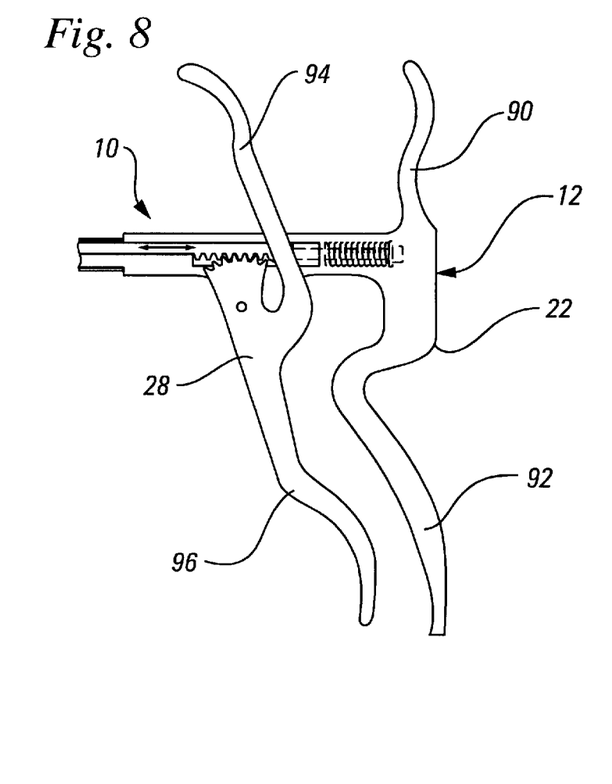
FIG. 8 is cut-away side view of a two handed embodiment of the invention in an actuated, cutting position.

In the embodiment shown in FIGS. 1–3, the proximal end 12 contains only one handle body lever 22 and one pinion lever 28. This embodiment is designed for single-handed operation. However, in at least one alternative embodiment, shown in FIGS. 7 and 8 the reamer tool may be designed for two-handed actuation. As may be seen, a two handed reamer tool 10 has a the proximal end 12 having a handle body lever 22 which is equipped with opposing grip portions 90 and 92, as well as a pinion lever 28 having opposed section 94 and 96 as well. The present embodiment of the reamer tool 10 may be designed in such a manner that in order to rotate the cutter 60 an two handed grip of alternating action is required to actuate the opposing grips and lever sections 90, 94 and 92, 96 respectively.

Figures 4, 5:
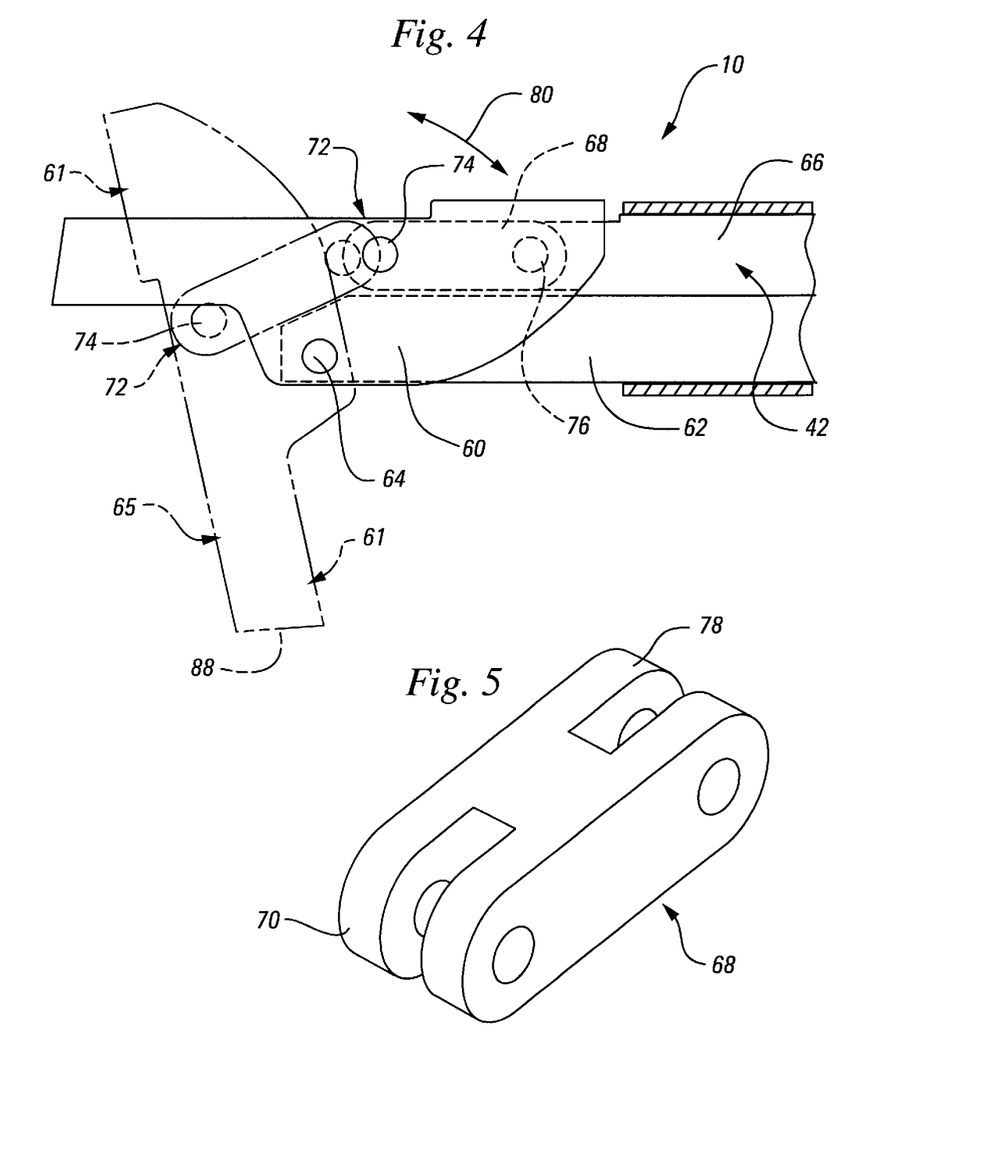
FIG. 4 is a side view of the distal end of an embodiment of the invention wherein the pivoting action of the cutter beam is illustrated.
FIG. 5 is a perspective view of the linkage assembly of the distal end of the reamer tool shown in FIG. 4.

Turning to FIG. 4, the distal portion or end 16 of the reamer 10 contains the reamer head or cutting beam 60. The beam has a plurality of cutting surfaces 61. In the embodiment shown, the cutting blades are located at the both ends 86 and 88 of the beam. The beam 60 is pivotally connected to a handle body extension 62 by a lower pivot member 64.

Figure 6:
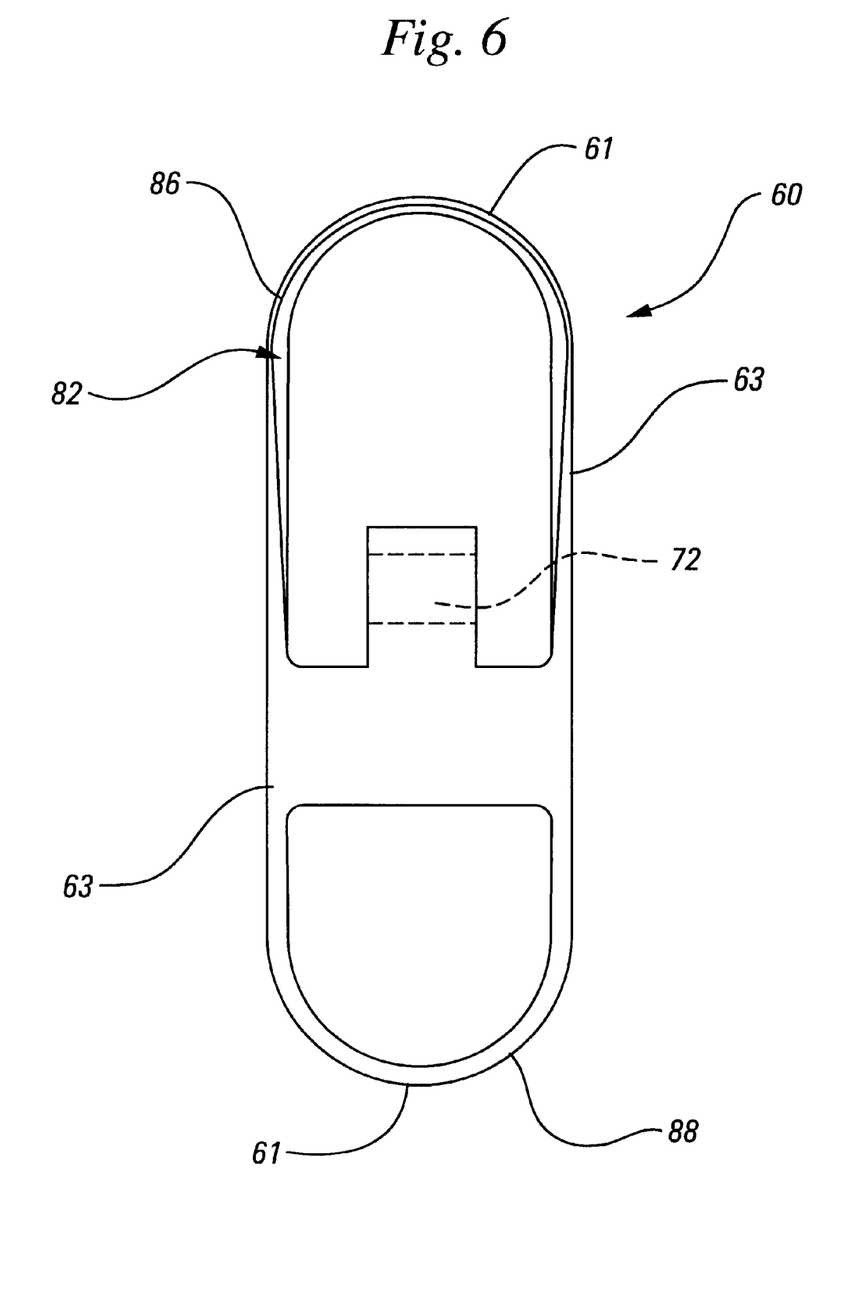
FIG. 6 is a top-down view of an embodiment of the cutter beam.

The beam 60 is also engaged to the distal end 66 of the drive rod 42 via linkage assembly 68. The linkage assembly 68 comprises a pair of beam engagement projections 70, as best shown in FIG. 5, which are disposed about the linkage tab 72 of the beam 60, as best shown in FIG. 6. As may be seen in FIG. 4, a proximal pivot member 74 passes through the linkage tab 72 and the beam engagement projections 70.

As may be seen in FIG. 5, the linkage assembly 68 also includes a pair of rod engagement projections 78. As shown in FIG. 4, a distal pivot member 76 passes through the pair of rod engagement projections 78 as well as the distal end 66 of the drive rod 42. As indicated by arrows 80, the unique arrangement of the beam 60 to the drive rod 42 and extension 62 via the linkage assembly 68 provides the reamer 10 with the ability to rotate the beam 60 about the lower pivot member 64 when the drive rod 42 is distally extended in the manner previously described. When the beam 60 is rotated, the cutting edges 61 will cut into and abrade any tissue which is encountered by the moving cutting edges 61.

As may be seen in FIG. 6, the cutting edges 61 are positioned on both ends 86 and 88 of the beam 60 and may be on opposing sides of the beam 60, such as may be seen in FIG. 4. In the present embodiment shown in FIG. 6, the cutting blades 61 may be curved about the shape of a semi-circle, however, the blades 61 may also be provided with other shapes as desired. In addition, the entire perimeter 82 of the beam 60, or a portion thereof, may include bladed portions 61 which extend beyond the semi-circle shape to form a "U" shape, such that cutting may occur along the lateral edges 63 of the perimeter 82 as well as the semi-circular ends 86 and 88. As a result, the reamer 10 may be configured to provide a variety of cutting options which will provide a smooth uniform resecting action as the beam 60 rotates back an forth as indicated by arrows 80 in FIG. 4.

In another embodiment of the invention the beam 60 may include one or more backward cutting blades 65, as is shown in FIG. 4, allowing cutting in both the forward and reverse directions.

The reamer 10 of the present invention may be used in a number of different manners as may be recognized by those of skill in the art. When employed to debride an interver-tebral disc, it may be understood that the reamer 10 may be used in the following manner.

After adequate exposure of a small portion of the disc is accomplished by the surgeon using well known standard techniques, any appropriately sized standard drill may be used to perforate the disc. The drill is guided in a direction that crosses the central portion of the disc, to a depth that comes close to, but does not penetrate the far side of the disc.

The distal end 16 of the reamer 10 is then placed into the disc to the full depth of the drilled hole. The reamer 10 is oriented such that its beam 60, with attached cutting blades 61, is parallel to the transverse plane of the disc.

The application of a manual compression force, such as by gripping the pinion lever 28 toward the handle body lever 22 forces the drive rod 42 in the distal direction. This causes the beam 60 to rotate in an elliptical manner around the lower pivot member 64. As is shown in FIG. 4, the beam 60 may be pivotally displaced at least 90 degrees when the pinion lever 28 is actuated such as may be seen in FIG. 3. The cutter will typically provide more than 100 degrees of cutting. This motion causes the cutting blades 61 (and 63) to move against any intervening tissue, cleanly cutting that tissue. The return spring 32 forces the drive rod 42 and the beam 60 back to their original and respective non-actuated positions when the pinion lever 28 is relaxed, such as may be seen in FIG. 2. This procedure may be used to remove the outer nucleus as well as the inner annulus of a spinal disk, leaving the outer annulus intact. Such a procedure is the goal of a partial disectomy. The reamer 10 may then be reoriented 180 degrees, so that the opposite side of the disc can be debrided.

Figure 9:
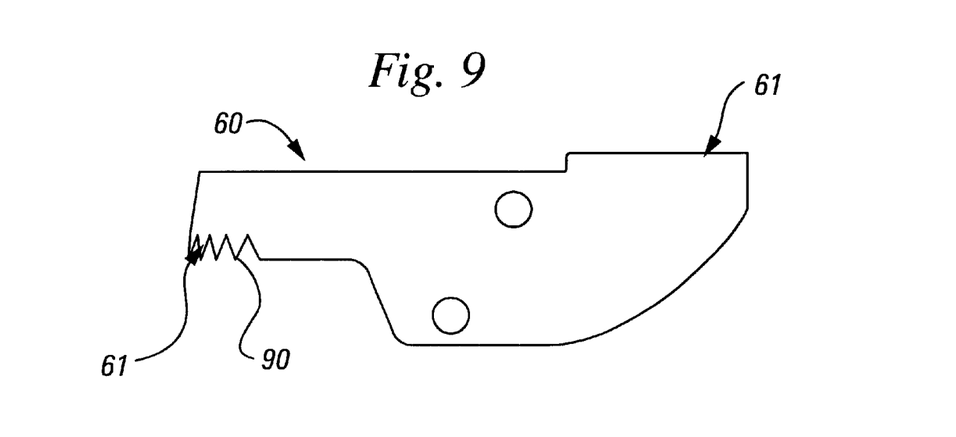
FIG. 9 is a side view of a serrated cutting beam.
Figure 10:
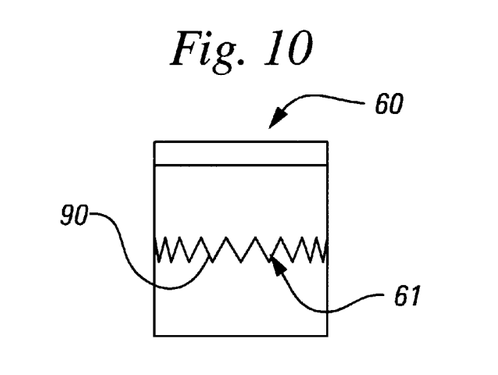
FIG. 10 is an end view of the serrated cutting beam of FIG. 9.

In addition, to providing the cutting motion described above, the present invention may also utilize a variety of blade types to provide for different cutting and resecting characteristics. For example, in FIGS. 4 and 6 the cutter beam 60 may be seen to employ one or more straight edge blades on the cutting edges 61. Alternatively, one or more of the cutting edges 61 may also have serrated teeth 90 such as may be seen in FIGS. 9 and 10.

Figure 11:
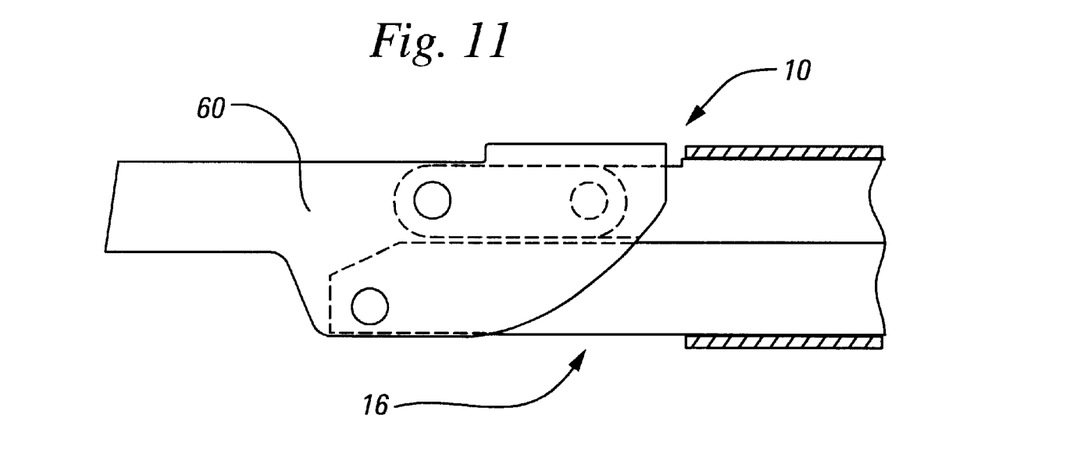
FIG. 11 is an enlarged side view of the end of the tool showing the cutting beam attachment.

As may best be seen in FIG. 11, when the reamer tool 10 is in the at rest or non-actuated position, the cutter beam 60 is maintained in a position such that the distal end 16 retains a profile substantially less than the distal end would have when in the actuated position such as is shown illustrated in phantom in FIG. 4. The reduced profile of the non-actuated distal end is sufficiently small to allow insertion of the distal end 16 into a small space or cavity 100 such as is shown in FIG. 12.

Figure 12:
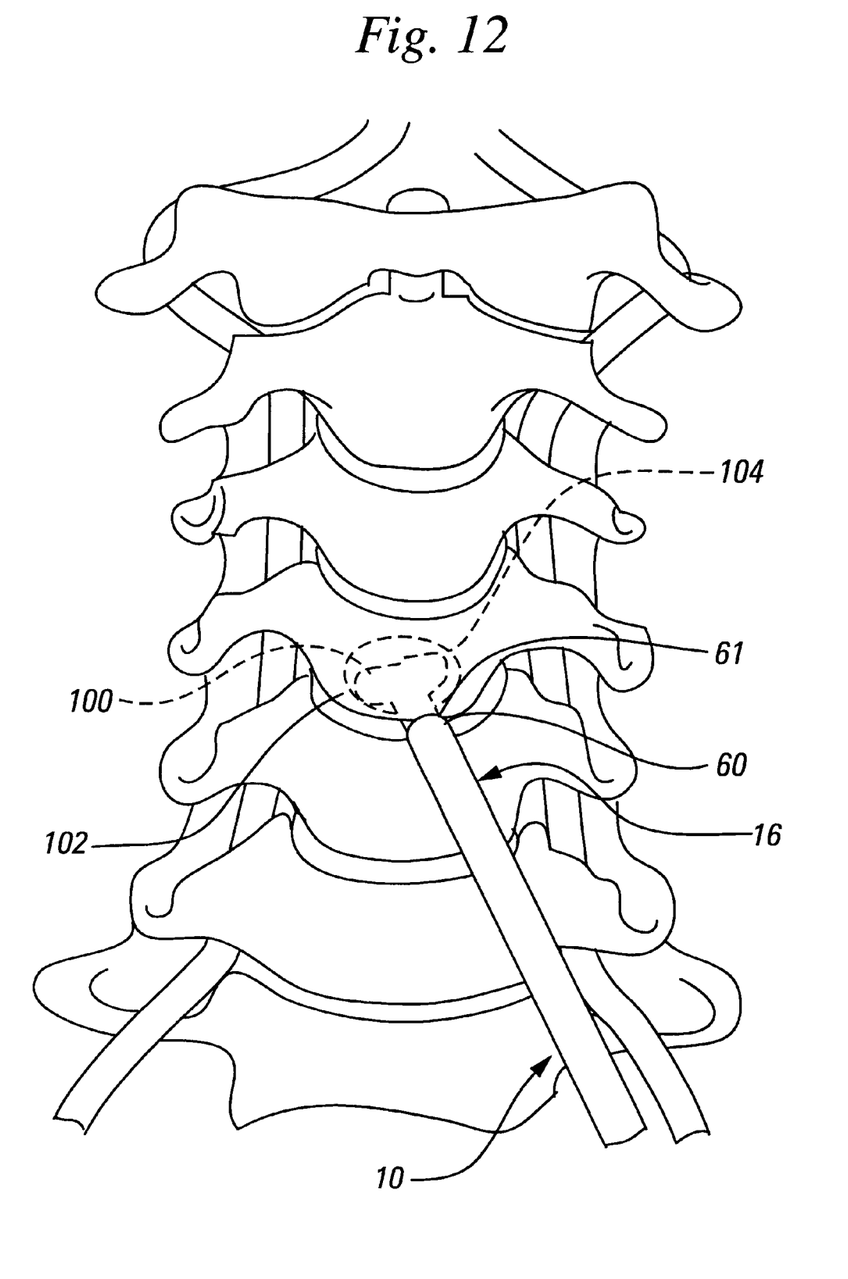
FIG. 12 is an anterior view of a spine showing a way in which the present invention may be used, without a guide tube over the tool.
Figure 13:
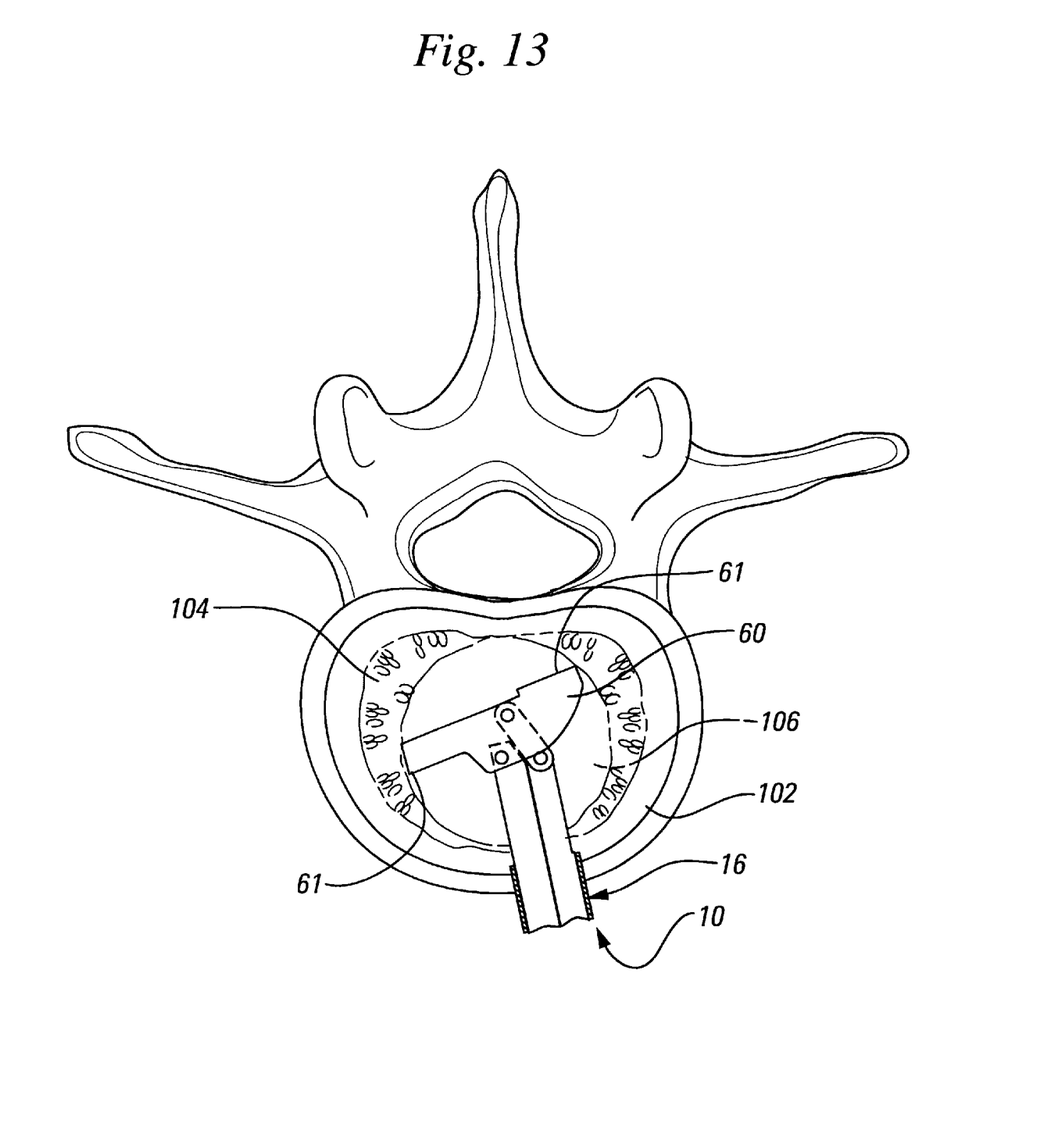
FIG. 13 is a top view of a vertebral body showing one location where the tool can enter and provide reaming.

In FIGS. 12–13, the reamer tool 10 is seen in use in merely one of a myriad of potential uses. As presently shown, the distal end 16 of the reamer tool 10 may be inserted into an opening or cavity 100 of a spinal body 102. As the cutter beam 60 is actuated, such as previously described, the cutting surfaces 61 abrade the surrounding tissue 104 to form a transverse cavity 106. Alternatively, the reamer tool 10 may be used to resect tissue from a spinal body 102 in the middle of a vertebral compression fracture, such as may best be seen in FIG. 14.

Figure 14:
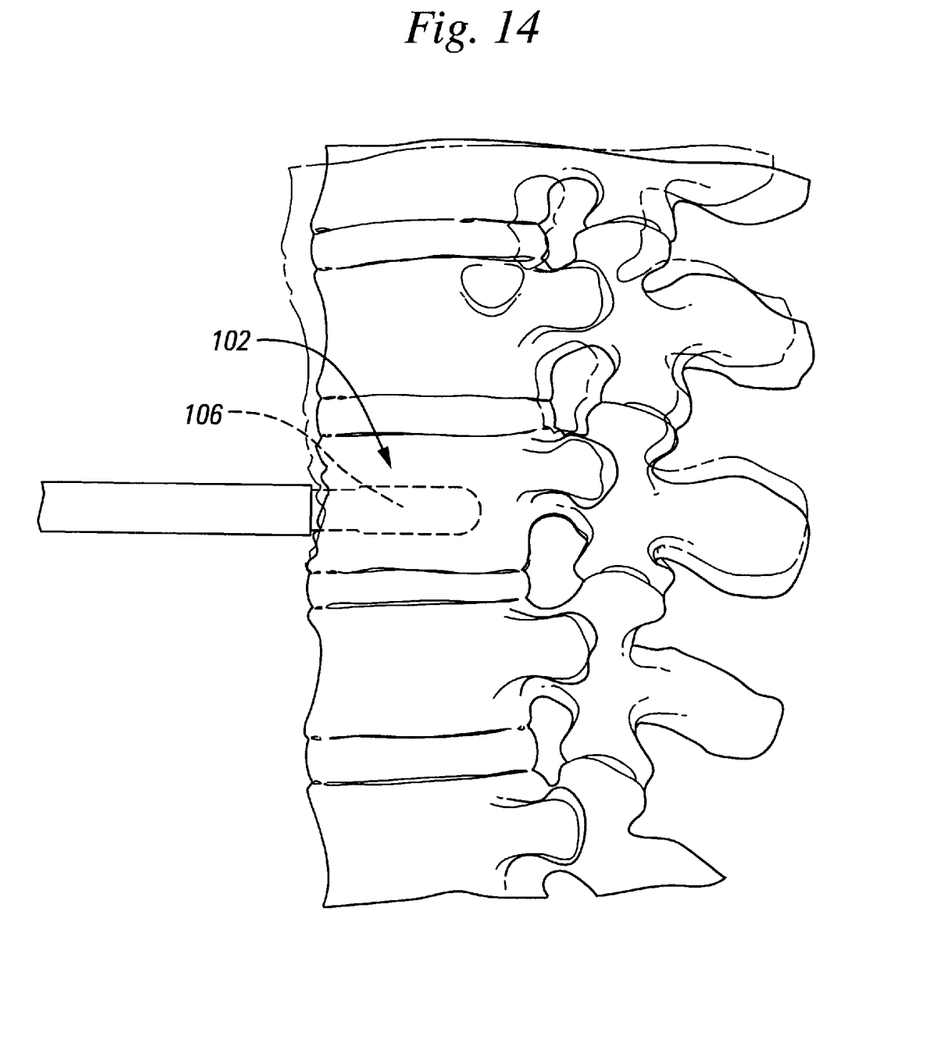
FIG. 14 is a side view of a spine section showing an alternative manner in which the present invention may be used.

After the cavity has been formed, the tool 10 along with any resected tissue is removed. The newly formed cavity may then be filled with filler material such as bone cement and/or graft material. The cavity created by the tool would tend to place the filler in a position where it could accumulate and develop pressure that would tend to elevate or re-expand (or reduce—in orthopedic terms—) the fracture, thereby forcing bone fragments into their pre-injury positions as illustrated in FIG. 14.

In addition to the uses described above, the various embodiments of the reamer tool 10 as described herein may also be used in a wide variety of other procedures. For example, the present reamer tool may be used for removing bone cement from the intramedullary canal of long bones during reconstructive procedures such as joint replacement. The tool may also be useful for debriding cartilage from joints during arthoscopic procedures. Another use may involve using the present reamer tool for certain types of joint arthrodesis, e.g. ankle, inter-tarsal, metatarsal-phalangeal, etc., wherein the tool is used in debriding and preparation of surfaces.

Other uses for the present invention may include: using the reamer tool for producing or sculpting channels for tendon insertion and/or reattachment, such as anterior curciate or rotator cuff repairs. The reamer tool may be used in nasal or sinus surgery for sub-mucosal resections. The reamer tool may also find use in certain gynecological procedures such as a dilation and curettage procedure (D&C). Yet another potential use for the present invention would be for fat immobilization during lipo-suction operations. In such a use the tool could be useful in freeing up fatty tissue to improve removal.

In addition to being directed to the embodiments described above and claimed below, the present invention is further directed to embodiments having different combinations of the features described above and claimed below. As such, the invention is also directed to other embodiments having any other possible combination of the dependent features claimed below.

The above examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. A tool for cutting tissue comprising:
   a body, the body having a drive rod constructed and arranged for longitudinal movement therethrough;
   a handle lever being operatively engaged to the drive rod, such that when the handle lever is moved between a first position and a second position the drive rod is moved between an advanced position and a retracted position, the drive rod extending from a proximal end of the body to a distal end; and
   a cutter beam, cutter beam being pivotally engaged to the distal end of the body, the cutter beam being pivotally moveable between a non-actuated position and an actuated position, a lower pivot member pivotally connects the distal end of the body and the cutter beam, the cutter beam being further pivotally engaged to a distal end of the drive rod, whereby when the drive rod is moved to the advanced position the cutter beam is pivoted about the lower pivot member to the actuated position and when the drive rod is moved to the retracted position the cutter beam is pivoted back to the non-actuated position, the cutter beam comprising a first cutting edge and a second cutting edge opposably mounted on the cutter wherein the first cutting edge is positioned on a front side of the cutter and the second cutting edge is positioned on a back side of the cutter, at least one of the first cutting edge and the second cutting edge being positioned to cuttingly engage surrounding tissue when the cutter is moved into the actuated position.

2. The tool of claim 1 wherein the handle lever is engaged to the drive rod in a rack and pinion arrangement.

3. The tool of claim 2 wherein the drive rod comprises a rack and the handle lever comprises a pinion.

4. The tool of claim 1 further comprising a linkage assembly, the linkage assembly having a first end and a second end, the first end being pivotally engaged to the distal end of the drive rod by a first pivot member, the second end pivotally engaged to the cutter beam by a second pivot member.

5. The tool of claim 1 further comprising a return mechanism, the return mechanism constructed and arranged to exert a predetermined force on the drive shaft, the predetermined force being sufficient to return the drive shaft to the retracted position when an outside force is not engaging the handle lever.

6. The tool of claim 5 wherein the return mechanism comprises:
   a shoulder bolt, the shoulder bolt having a bolt shaft and an end portion, the shoulder bolt being at least partially contained within the body, a biasing member is disposed about at least a portion of the bolt shaft, the bolt shaft being engaged to a proximal end of the drive shaft, the end portion sized to retain the biasing member about the bolt shaft, the bolt shaft passing through a return member, the return member being engaged to the body, the return member constructed and arranged to prevent passage of the biasing member therethrough but to allow the bolt shaft to pass therethrough.

7. The tool of claim 1 wherein the at least one of the first cutting edge and the second cutting edge is positioned to cuttingly engage the surrounding tissue when the cutter is moved from the actuated position to the non-actuated position.

8. The tool of claim 1 wherein the at least one of the first cutting edge and the second cutting edge is straight.

9. The tool of claim 1 wherein the at least one of the first cutting edge and the second cutting edge is curve.

10. The tool of claim 1 wherein the at least one of the first cutting edge and the second cutting edge is U-shaped.

11. The tool of claim 1 wherein the at least one of the first cutting edge am the second cutting edge is serrated.

12. A method of cutting tissue comprising the following steps:
    a) providing a resecting reamer tool, the tool comprising:
       a body, the body having a drive rod constructed and arranged for longitudinal movement therethrough;
       a handle lever being operatively engaged to the drive rod, such that when the handle lever is moved between a first position and a second position the drive rod is moved between an advanced position and a retracted position, the drive rod extending from a proximal end of the body to a distal end;
       a cutter beam, cutter beam being pivotally engaged to the distal end of the body, the cutter beam being pivotally moveable between a non-actuated position and an actuated position, a lower pivot member pivotally connects the distal end of the body and the cutter beam, the cutter beam being further pivotally engaged to a distal end of the drive rod, whereby when the drive rod is moved to the advanced position the cutter beam is pivoted about the lower pivot member to an actuated position and when the drive rod is moved to the retracted position the cutter beam is pivoted back to the non-actuated position;
    b) providing an opening into a spinal disk;
    c) placing the distal end of the body into the opening;
    d) orienting the tool such that the cutter beam oriented in a substantially parallel manner to a transverse plane of the disc;
    e) applying a manual compression force to the handle lever, thereby moving the handle from the first position to the second position, the drive rod from the retracted position to the advanced position and the cutter beam from the non-actuated position to the actuated position;
    f) cutting any tissue which is engaged by the cutter beam;
    g) removing the manual compressive force from the handle lever; and
    h) returning the handle from the second position to the first position, thereby moving the drive rod from the advanced position to the retracted position and moving the cutter beam from the actuated position to the non-actuated position.

13. The method of claim 12 wherein steps e) through h) are repeated until a desired amount of tissue is removed from the spinal disk.

14. A tool for cuffing tissue comprising a housing, a shaft, a beam, and an activation member
    the housing being at least partially disposed about the shaft the shaft constructed and arranged to moved proximally and distally within the housing;
    the beam being pivotally engaged to a distal end of the shaft, the beam constructed and arranged to be rotated about a pivot member engaged to the distal end of the shaft and the beam, the beam having at least two cuffing blades, each cutting blade being positioned at opposite ends of the beam, wherein at least one of the at least two cutting blades is positioned on a front side of the beam and at least one of the at least two catting blades is positioned on a back side of the beam; and
    the activation member being operatively engaged to the proximal end of the shaft, when the activation member is placed in an activated position the shaft is moved distally relative to the housing thereby pivoting the beam in a predetermined arc about the pivot member.

* * * * *